United States Patent [19]

Harris

[11] Patent Number: 4,716,146

[45] Date of Patent: Dec. 29, 1987

[54] 4-ALKYLPHENYL-2-ALKOXYETHYL ETHERS AND FRAGRANCE COMPOSITIONS CONTAINING SAME

[75] Inventor: Eugene G. Harris, West Chester, Ohio

[73] Assignee: National Distillers and Chemical Corporation, New York, N.Y.

[21] Appl. No.: 944,143

[22] Filed: Dec. 19, 1986

Related U.S. Application Data

[63] Continuation-in-part of Ser. No. 636,772, Aug. 1, 1984, abandoned.

[51] Int. Cl.$^4$ .......................... A61K 7/46; C11B 9/00; C07C 43/20
[52] U.S. Cl. ........................................ 512/21; 568/648
[58] Field of Search ...................... 568/648; 252/522 R

[56] References Cited

U.S. PATENT DOCUMENTS

| | | | |
|---|---|---|---|
| 2,451,149 | 10/1949 | Neil et al. | 568/648 |
| 2,620,359 | 12/1952 | Britton et al. | 568/648 |
| 4,362,557 | 12/1982 | Kiwala et al. | 252/522 R |
| 4,404,407 | 9/1983 | Harris | 568/648 |

FOREIGN PATENT DOCUMENTS 0018524  2/1978  Japan .................... 568/648

*Primary Examiner*—Werren B. Lone
*Attorney, Agent, or Firm*—Kenneth D. Tremain; Gerald A. Baracka

[57] ABSTRACT

This invention relates to compounds of the general structure

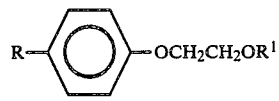

wherein R and R$^1$ are lower alkyl having from 1 to 2 carbon atoms useful as fragrance additives and to the fragrance compositions containing the same.

6 Claims, No Drawings

4-ALKYLPHENYL-2-ALKOXYETHYL ETHERS AND FRAGRANCE COMPOSITIONS CONTAINING SAME

CROSS-REFERENCE TO RELATED APPLICATION

This application is a continuation-in-part of my copending application, Ser. No. 636,772, filed Aug. 1, 1984, now abandoned.

BACKGROUND OF THE INVENTION

This invention relates to novel fragrance compounds and more particularly, to novel 4-alkylphenyl-2-alkoxyethyl ethers and to fragrance compositions containing the same.

While many natural perfume chemicals, such as essential oils, oil of rose and oil of cloves, and animal secretions, such as musk, are known, a large number of synthetic odoriferous chemicals possessing aroma characteristics have been developed. Synthetic aroma chemicals have added a new dimension to the art of perfuming, since these synthetics are usually stable compounds and are relatively inexpensive, as compared with the natural perfume chemicals. For example, ethylene glycol monoaryl ethers of the general formula:

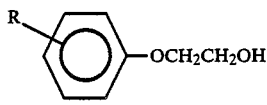

are known fragrance compounds having a mild rose odor and are useful for food, cosmetic and pharmaceutical applications. See, for example, U.S. Pat. Nos. 1,881,200, 2,451,149 and 4,404,407. Moreover, synthetics lend themselves more easily to manipulation than natural perfume chemicals since natural perfume chemicals are usually a complex mixture of substances. Accordingly, for these and other reasons, there is a great desire in the art of fragrance chemistry for new compounds possessing specific characteristic aromas.

Japanese Pat. No. 53-18524 discloses compounds of the formula:

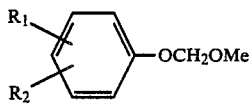

wherein $R_1$ and $R_2$ are hydrogen, halogen or lower alkyl. These compounds are stated to have bactericidal activity. In aqueous media, these masked acetals will be in equilibrium with formaldehyde, methanol, and the respective substituted cresols.

Bactericidal agents, such as Germall 115 ®, 3-hydroxymethyl-5,5-dimethylhydantoin, and 2-nitro-2-bromo-1,3-propanediol, are known or thought to be formaldehyde releasing agents. Formaldehyde has been shown to produce nasal tumors in rats and as a result debate continues whether products which may contain formaldehyde should have warning labels or be limited in use or exposure. Therefore, it would not be prudent to utilize a potential formaldehyde releasing compound for fragrance applications.

Chemical Abstracts 54:365 (1960) also discloses, inter alia, compounds of the formula:

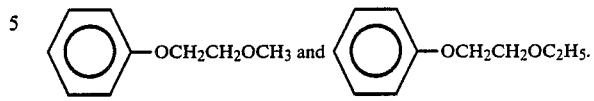

Neither of these references disclose that these compounds or derivatives thereof have fragrance qualities useful as additives in fragrance compositions.

SUMMARY OF THE INVENTION

It is an object of the present invention to provide novel synthetic fragrance compounds.

Another object of this invention is to provide fragrance compositions utilizing novel synthetic aroma compounds.

Still another object of the present invention is to provide novel aroma compounds utilized in the preparation of fragrances and fragrance compositions.

These and other objects are achieved herein by providing novel 4-alkylphenyl-2-alkoxyethyl ether compounds having the general formula

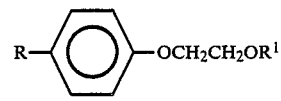

wherein R and $R^1$ are lower alkyl having from 1 to 2 carbon atoms. These compounds are characterized with a pleasant natural green foliage note and are employed herein as fragrance additives in fragrance compositions.

DETAILED DESCRIPTION OF THE INVENTION

In accordance with the present invention, it has been found that the above described novel 4-alkylphenyl-2-alkoxyethyl ethers have a very pleasant natural green foliage note very similar to natural privet. More particularly, the novel 4-alkylphenyl-2-alkoxyethyl ethers of the present invention, also sometimes referred to as 2-alkyoxyethoxy-4-alkylbenzenes, which possess this desirable property have the general formula

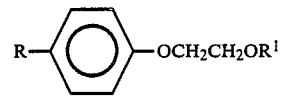

wherein R is methyl or ethyl, and $R^1$ is also methyl or ethyl. Preferably R and $R^1$ are methyl. Thus a most preferred compound within the scope of the present invention is 4-methylphenyl-2-methoxyethyl ether.

The novel compounds of the present invention can be prepared by a variety of techniques. For example, one method involves the reaction of p-alkylphenols, e.g., p-cresol, with haloethylalkyl ethers, e.g. chloroethylmethyl ether, in the presence of alkali hydroxide, such as sodium hydroxide. Another technique involves reacting p-alkylphenols, e.g. p-cresol, with ethylene oxide in the presence of potassium hydroxide and sodium borohydride. The 4-alkylphenoxyethanol is then reacted with a dialkylsulfate, such as dimethylsulfate, in the presence of sodium hydroxide and tetrabutylammonium iodide, or methyl chloride in the presence of sodium or potassium hydroxide at 60°–100° C. The odor characteristics of the desired compounds of the present invention are independent of the synthetic route.

As a result of their pleasing aroma, the novel compounds of the present invention are useful as fragrances in the preparation and formulation of fragrance compositions, such as perfumes, and perfumed products. Thus, the term fragrance compositions is intended herein to mean products such as perfume and perfume products such as soaps, washing agents, dishwashing and other detergents, air fresheners and room sprays, toilet preparations, pomanders, candles, cosmetics, such as creams, colognes, pre- and after-shaving lotions, talcum powder, hair care agents, body deodorants and antiperspirants. The novel compounds of this invention can be utilized as the primary fragrance in many such compositions or may be combined with other compatible fragrances. The compounds of this invention have good stability in acidic cleaners and oxidative cleaners (bleaches) and impart a green odor to the formulation.

In most applications, the compounds of this invention can be used in amounts from about 0.01 to about 15% by weight, preferably 0.1 to about 10% by weight of the fragrance composition.

Accordingly, the following examples are presented by way of illustration and not by way of limitation so that those skilled in the art may better understand how to practice the invention.

EXAMPLE 1

4-Methylphenyl-2-methoxyethyl ether is obtained by reacting p-cresol and chloromethylethyl ether in accordance with the equation:

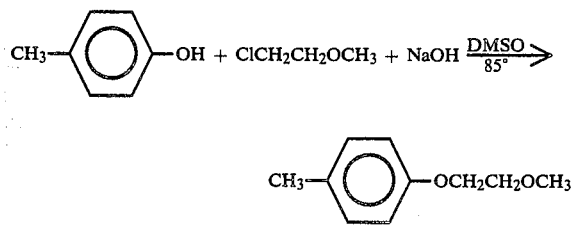

For the reaction, 113.9 gms. (1.055 moles, 110.2 mls.) of p-cresol, 84.4 gms. (2.11 moles) of NaOH and 319 mls. of dimethyl-sulfoxide (DMSO) are charged to a 2-liter flask fitted with a mechanical stirrer, condenser, thermometer and addition funnel. The mixture is heated to 85° C. for 1 hour and 200 gms. (2.11 moles, 193 mls.) of chloromethylethyl ether are then added to the reaction mixture over a period of 2 hours. When the addition is complete the reaction mixture is heated at 85° C. for 3 hours. A sample is removed for gas chromatographic (GC) analysis and shows essentially 100% conversion of the p-cresol to the desired 4-methylphenyl-2-methoxyethyl ether. Sufficient water is then added to the reaction mixture to dissolve salts and the organic and aqueous layers separated. The organic portion is then take up in either and the water layer extracted with ether and the combined ether solutions dried over MgSO4. Filtration and removal of the ether solvent yields 184 gms crude 4-methylphenyl-2-methoxyethyl ether. The crude product is vacuum distilled using a 6″ Vigreaux column to obtain 167 grams (95.4% yield) pure 4-methylphenyl-2-methoxyethyl ether [B.P. 70° C. at 0.6 mm Hg; Specific gravity (25°/25° C.) 1.0090; Color 98/99 (% trans. at 440/550 nm)]. The structure of the product is confirmed by infrared and proton nuclear magnetic resonance spectroscopy:

IR (neat) 1235 cm$^{-1}$, C—O—C, 1250 cm$^{-1}$, Ar—O—C.

NMR (CDCl$_3$) δ 2.24 (S, 3, ArC—H), 3.4 (S, 3, —OCH), 3.55–4.25 (M, 4, OCH—CH—O), 6.76–7.2 (M, 4, Ar—H).

EXAMPLE 2

This example illustrates another technique to prepare 4-methylphenyl-2-methoxyethyl ether. The reaction is represented by the equation:

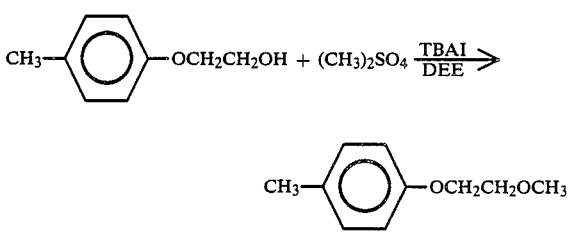

For this reaction, 50 gms. (0.33 mole) of 4-methylphenoxyethanol ethanol and 2.43 gms. (0.0066 mole, 2 mole %) of tetrabutylammonium iodide (TBAI) are charged with 100 mls diethylether (DEE) to a 500 ml. flask fitted with mechanical stirrer, condenser, addition funnel and N$_2$ inlet. Sixty-six gms. (1.65 moles) of sodium hydroxide (as a 50% aqueous solution) are then added to the flask over 15 minutes and the mixture stirred by 178 hour. Dimethyl sulfate (108 gms; 81 mls; 0.86 mole) are added to the viscous mixture over a period of one hour and the reaction mixture becomes less thick as addition nears completion. When the addition is complete, the mixture is stirred for two hours. The reaction mixture is combined with 150 mls. of distilled water. The organic layer is washed three times with water and, after the addition of more diethyl ether, dried over MgSO$_4$. Filtration and removal of solvent affords 50 gms. crude product (98.3% 4-methylphenyl-2-methoxyethyl ether). Distillation of the crude material yields pure 4-methylphenyl-2-methoxyethyl ether (B.P. 65° C. at 0.25 mm Hg). The infrared and proton nuclear magnetic resonance spectra are in agreement with the data presented in Example 1 and confirm the structure of the product.

The 4-methylphenyl-2-methoxyethyl ether obtained via the above-described procedures has a natural leaf green odor. The complex odor properties include, but are not limited to, those found in phenylacetaldehyde, dimethylacetal and 3-phenylpropyl alcohol. Nuances of lilac, Elang and rose are evident in the odor profile.

EXAMPLE 3

Comparative example—not part of the present invention

4-Methylphenyl methoxymethyl ether is obtained by reacting p-cresol and chloromethylmethyl ether following essentially the teachings of Japanese Patent No. 53-18524 in accordance with the equation:

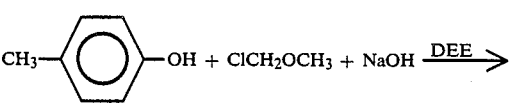

-continued

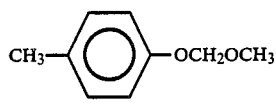

For this reaction sodium hydride (60 gms.) is washed twice with hexane in a 500 ml. flask fitted with a mechanical stirrer, condenser, thermometer, water bath and addition funnel. Diethyl ether (500 ml) is then added. p-Cresol (138.9 grams, 1.24 moles) is added with the temperature maintained at 25° C. Chloromethylmethyl ether (100 gms, 1.24 moles) is then added over a two hour period with the temperature maintained between 20°–25° C. The reaction is stirred for 4 hours. A neutralized sample is removed for gas chromatographic (GC) analysis and shows 60% conversion of the p-cresol to the desired 4-methylphenyl methoxymethyl ether. After stirring for two more hours another sample is taken and by gas chromatographic analysis shows no further conversion. Sufficient water is then added to the reaction mixture to dissolve the salts and the organic and aqueous layers are separated. The organic layer is washed twice with 200 ml portions of water and then reduced on a rotovap after drying with $Na_2SO_4$. The crude material is then vacuum distilled through a packed column and separated into three fractions.

A portion of the first distillation cut which contained 87 percent 4-methylphenyl methoxymethyl ether is combined with an equal amount of 10 percent aqueous hydrochloric acid. After two hours, gas chromatographic analysis of the organic layer showed that it contained 55 percent product, 31 percent unknown, and 12 percent cresol. After stirring for 48 hours, the organic layer contained 41 percent product, 20 percent unknown, and 25 percent cresol. After stirring for three additional days, gas chromatographic analysis showed it to contain only 4 percent product, 20 percent unknown breakdown materials and 70 percent cresol. The above data demonstrates the instability of the 4-methylphenyl methoxymethyl ether product.

By contrast, when a sample of the product of the present invention, 4-methylphenyl-2-methoxyethyl ether is stirred with an equal weight of 10 percent aqueous hydrochloric acid solution for three days no change in the odor character or composition when analyzed by gas chromatographic analysis is noted.

A portion of the second distillation cut which is 99.8 percent pure 4-methylphenyl methoxymethyl ether is rinsed with 10 weight percent of a 10 percent aqueous sodium hydroxide solution to eliminate the remaining traces of cresol and the structure confirmed by proton nuclear magnetic resonance spectroscopy:

NMR ($CDCl_3$) δ: 2.274 (S, 3, Ar C—H), 3.447 (S, 3, —OCH), 5.120 (S, 2, OCH—O)

Upon evaluation by an expert perfumer, the cresol-free product had no apparent floral or natural green foliage characteristics but rather possessed a strong cresolic-like odor. As a consequence, the 4-methylphenyl methoxymethyl ether is not suitable as a fragrance additive whereas the 4-methylphenyl-2-methoxyethyl ether of the present invention surprisingly possesses a natural green foliage note very similar to natural privet.

EXAMPLE 4

The preparation of fragranced soap bars is illustrated by this example wherein soaps are prepared by the Mazzoni process. For each run, 1800 gms. of a commercial non-scented soap stock and 1% by weight of fragrance chemical are used. Water is added as required during the processing to provide the necessary plasticity. The 4-methylphenyl-2-methoxyethyl ether is added to the soap stock and thoroughly blended in before the soap stock is extruded in a tubular form. Fragranced soap bars are then stamped from sections of the extruded tube.

The bars prepared in this manner had odor properties similar to neat 4-methylphenyl-2-methoxyethyl ether.

EXAMPLE 5

A sample of 4-methylphenyl-2-methoxyethyl ether is mixed with a household bleach solution (5.25% NaOCl by weight). The sample had a more pleasant, less chemical odor than the unfragranced bleach sample. The fragranced bleach and a control (unfragranced) bleach solution were stored in the dark and the amount of NaOCl in each sample is determined by iodometric analysis after 2 days and 6 days. Duplicate analyses were run for each sample. Results show the 4-methylphenyl-2-methoxyethyl ether to have no effect on the degradation of the bleach within the experimental limitations of analysis and the fragranced bleach solution suffered no odor change.

EXAMPLE 6

4-Methylphenyl-2-methoxyethyl ether is adsorbed on a cosmetic grade talc at a 0.1 weight percent level. More of the natural green rose character of the product is evident when placed on the talc. A small portion of the fragranced talc is subjected to ultraviolet radiation for eight hours and there is no noticeable discoloration or change in odor characteristics. Another portion of the fragranced talc is stored at 45° C. for two weeks in a closed container without discoloration or change in odor characteristics.

EXAMPLE 7

4-Methylphenyl-2-methoxyethyl ether is added to an herbal perfume base at a 10 weight percent level to enhance the natural green characteristics of the formulation. Incorporation of the perfume base in a shampoo and bar soap provides products having a very natural herbal, fresh odor with good persistence.

EXAMPLE 8

A toilet bowl cleaner is prepared by combining and thoroughly mixing the following:

|  | Parts by Weight |
| --- | --- |
| 20° Baume Hydrochloric Acid | 120 |
| Tricaprylylmethylammonium Chloride | 4 |
| Imidazoline of Coconut Fatty Acids | 4 |
| Nonylphenoxy Polyethoxyethanol | 8 |
| Water | 264 |
|  | 400 |

An aliquot of the solution is removed and 1 weight percent 4-methylphenyl-2-methoxyethyl ether added thereto. The resulting fragranced toilet bowl cleaner preparation has a natural, fresh scent.

EXAMPLE 9

A fragranced detergent is prepared by adsorbing 0.01 weight percent 4-methylphenyl-2-methoxyethyl ether on a commercially available unfragranced detergent. The fragranced detergent thus prepared has a pleasant fresh odor. When the fragranced detergent is mixed into warm water, a pleasant fresh green odor is noted.

EXAMPLE 10

A liquid soap is prepared in accordance with the following formulation:

|  | Parts by Weight |
|---|---|
| Emersal ® 6400 Sodium Lauryl Sulfate | 30.0 |
| Emid ® 6511 Lauramide DEA | 6.0 |
| Lanoquat ® 1756 Lanolin Quaternary | 1.0 |
| Emerest ® 2350 Glycol Stearate | 1.0 |
| Emersol ® 132 Stearic Acid | 0.5 |
| Triethanolamine | 0.3 |
| Emeressence ® 1160 Rose Ether ™ Phenoxyethanol | 1.0 |
| Deionized Water | 60.2 |
|  | 100.0 |

The ingredients are combined and heated slowly to 75° C. until all of the components melt. The mixture is then cooled to 40° C. with agitation and 0.5 weight percent 4-methylphenyl-2-methoxyethyl ether blended into the formulation. The resulting liquid soap preparation has a very natural herbal odor.

EXAMPLE 11

A mild shampoo base is prepared in accordance with the following recipe:

|  | Parts By Weight |
|---|---|
| Emersal ® 6455 Sodium Laureth Sulfate | 20.0 |
| Emery ® 5320 Laureth Sulfosuccinate | 10.0 |
| Emid ® 6515 Cocamide DEA | 5.0 |
| Emery ® 5412 Cocoamphoglycinate | 4.0 |
| Emeressence ® 1160 Rose Ether ™ Phenoxyethanol | 0.7 |
| Deionized Water | 60.3 |

-continued

|  | Parts By Weight |
|---|---|
|  | 100.0 |

The ingredients are combined and heated with agitation until a homogeneous blend is obtained. Viscosity and pH are then adjusted by the addition of small increments of sodium chloride and citric acid, respectively. One-half weight percent 4-methylphenyl-2-methoxyethyl ether is then blended into the shampoo base. The resulting shampoo has a very pleasant natural herbal odor.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A compound having the structural formula:

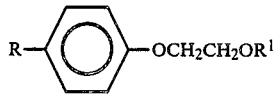

wherein R and $R^1$ are lower alkyl having from 1 to 2 carbon atoms.

2. The compound of claim 1 wherein R and $R^1$ are methyl.

3. A fragrance composition having incorporated therein an odoriferous amount of a compound defined in claim 1.

4. A fragrance composition having incorporated therein an odoriferous amount of a compound as defined in claim 2.

5. A process for enhancing or improving the fragrance properties of perfumes and perfumed products which comprises incorporating therein an odoriferous amount of the compound defined in claim 1.

6. A process for enhancing or improving the fragrance properties of perfumes and perfumed products which comprises incorporating therein an odoriferous amount of the compound defined in claim 2.

* * * * *